United States Patent [19]

Scheinmann et al.

[11] Patent Number: 5,750,381
[45] Date of Patent: May 12, 1998

[54] ENZYMATIC PROCESS FOR MAKING MORPHINE-6-GLUCURONIDE OR SUBSTITUTED MORPHINE-6-GLUCURONIDE

[75] Inventors: Feodor Scheinmann, Sale; Nicholas John Turner, Devon; Neil Edward Carter, Manchester; Richard Talbot Brown, Preston, all of United Kingdom

[73] Assignee: Salford Ultrafine Chemicals and Research Limited, Manchester, England

[21] Appl. No.: 659,047

[22] Filed: Jun. 3, 1996

Related U.S. Application Data

[63] Continuation of PCT/GB94/02605, Nov. 29, 1994 published as WO95/16050, Jun. 15, 1995.

[30] Foreign Application Priority Data

Dec. 7, 1993 [GB] United Kingdom .................. 9325065

[51] Int. Cl.$^6$ .................. C12P 13/00; C12N 9/24
[52] U.S. Cl. .................. 435/128; 435/200
[58] Field of Search .................. 435/128, 200

[56] References Cited

PUBLICATIONS

Brown et al., Sybthesis of morphine–6–glucuronide via a highly selective catalysed hydrolysis reaction, Tetrahedron Letters, vol. 36(7), pp. 1117–1120, Feb. 13, 1995.

Primary Examiner—John L. LeGuyader
Assistant Examiner—Andrew Wang
Attorney, Agent, or Firm—Thomas W. Tolpin

[57] ABSTRACT

A method of making morphine-6-glucuronide comprising the selective enzymatic cleavage of the 3-glucuronide moiety in morphine-3, 6-glucuronide or substituted morphine-6-glucuronide using at least one β-glucuronide.

2 Claims, No Drawings

ENZYMATIC PROCESS FOR MAKING MORPHINE-6-GLUCURONIDE OR SUBSTITUTED MORPHINE-6-GLUCURONIDE

This application is a continuation of PCT/GB94/02605, filed Nov. 29, 1994, published as WO95/16050, Jun. 15, 1995.

This invention relates to an enzymatic process for making morphine-6-glucuronide or substituted morphine-6-glucuronide.

Morphine-6-glucuronide (also known as morphine-6-β-D-glucuronide and M-6-G) is a metabolite of morphine in the human body and is a more powerful analgesic than morphine itself (R. Osborne et. al., *The Lancet*, 1988, 828 and the literature cited therein). It has previously been synthesised by H. Yoshimura et al., (*Chem. Pharm. Bull.*, 1968, 16, 2114) and others eg P. A. Carrupt et al., (*J. Med. Chem.*, 1991, 34, 1272) using the Koenigs-Knorr procedure whereby methyl (m-O-acetyl-D-glucopyranosylbromide) uronate is synthesised (G. N. Bollenbach et al., *J. Amer. Chem. Soc.*, 1955, 77, 3310) and reacted with 3-acetylmorphine in the presence of silver carbonate in refluxing benzene. The final isolation of morphine-6-glucuronide requires liberating it from an insoluble barium slat prior to purification by recrystallisation (H. Yoshimura et al. *Chem. Pharm. Bull.*, loc. cit. and P. A. Carrupt et al., *J. Med. Chem.*, loc. cit.). Morphine-6-glucuronide is now required in substantial quantities for extensive biological and clinical evaluations. The trace amounts of heavy metals from the Koenigs-Knorr method of production can be very difficult to remove in the final product. Another problem associated with the Koenigs-Knorr reaction is that glycoside formation involves an unstable sugar derivative and a heterogeneous reaction system which leads to variable yields of the conjugate and difficulties in purification when the synthesis of morphine-6-glucuronide is carried out on larger scale.

Similar problems were encountered on producing morphine-3,6-diglucuronide (M-3,6-diG). This compound is also of importance as a metabolite or morphine and its monoglucuronides.

WO 93/03051 describes a method for making morphine-6-glucuronide derivatives by conjugating an optionally substituted glucuronide ester with optionally substituted morphine using acid catalysts.

The present invention seeks to provide an alternative method for making morphine-6-glucuronide or substituted morphine-6-glucuronide.

According to the present invention there is provided a method for making morphine-6-glucuronide by selective enzymatic cleavage of the 3-glucuronide moiety in morphine-3,6-glucuronide or substituted morphine-3,6-glucuronide using at least one β-glucuronidase.

Suitable β-glucuronidases include the following:

Abalone entrails—from the abalone mollusc
L-11—from the limpet *Patella vulgata*
HA-4—from *Helix aspersa*
H-5—from *Helix pomatia*
B-1—from bovine liver
B-3—from bovine liver
B-10—from bovine liver
BI—an insoluble enzyme from bovine liver suspended on beaded agarose
S-1—from the scallop *Chlamys opercularis*

The primary screening experiments were carried out in 0.1N citrate buffer with 1–2 mg/ml of the M-3,6-diG and 1–13,000 Fishman units of enzyme. One Fishman unit is the amount of enzyme required to liberate 1 μg of phenolpthalein from phenolphthalein glucuronide in one hour at 37° C. at a stated pH.

Successful experiments were carried out using M-3,6-diG with purity ranging from 80 to 96% which contained three other morphine glycosides.

The preliminary screening experiments yielded four enzymes that were particularly successful in selectively cleaving the 3-glucuronide. These included the following:

B-10

HA-4

L-11

Abalone entrails

However, the activity of the B-10 enzyme was relatively low. Both L-11 and HA-4 could tolerate M-3,6-diG at up to 17 mg/ml at low enzyme concentration whereas abalone entrails was inhibited at these levels. The enzyme concentrations were kept low to prevent any enzyme concentration inhibition. Further studies of L-11 and HA-4 showed that they could both tolerate up to 100 mg/ml of M-3,6-diG and 71,000 Fishman units/ml of enzyme without inhibition.

At high concentrations of M-3,6-diG L-11 seemed more effective at dealing with the impurities present than HA-4. L-11 was supplied with an activity of 1–3 million Fishman units per gram whereas the available HA-4 had an activity of only 0.25–0.50 million units per gram.

At the next stage of development, a target of at least 80% conversion to M-6-G was set since at this level the product could be purified by crstallisation. To this end the concentration of M-3,6-diG was set at 10 mg/ml and the concentration of L-11 varied. These experiments showed that a conversion of 94% in 24 hours could be obtained using 51,200 Fishman units/ml of L-11, and that above this concentration, activity was inhibited. Analysis of samples taken during the reaction showed that the enzyme had lost most of its activity after the first eight hours.

The next stage of the programme was to develop a method of stabilising the enzyme so that its activity would not be lost in the first eight hours, and to explore the possibility of recycling the enzyme. To this end, the enzyme was loaded onto oxirane acrylic beads in 0.1N acetate buffer before the M-3,6-diG was added. For these experiments the M-3,6-diG concentration was kept at 25–27 mg/ml, the L-11 concentration at 13,500 to 14,600 units and the amount of acrylic beads varied to establish the amount required to stabilise the enzyme. These experiments showed that the optimum level of acrylic beads was 50 mg per 14,600 Fishman units of enzyme. Using the supported enzyme, 14,600 Fishman units acting on 26 mg of M-3,6-diG could produce a 93% conversion in 71 hours. This rate of conversion would require about ten times as much enzyme if unsupported. The stability of the enzyme was so dramatically enhanced that it was still active after 71 hours, and when filtered off and washed, still retained almost half of its original activity.

This system was used on a gram scale and gave the desired product in 20–25% yield and high purity.

EXPERIMENTAL

Experimental data for supported L-11 in pH 3.8 acetate buffer

| Enzyme (U/ml) | M-3,6-diG (mg/ml) | Conversion to M-6-G | Acrylic beads (mg/ml) |
|---|---|---|---|
| 13,400 | 26 | 62% in 41 hours | 125 |
| 14,000 | 27 | 86% in 71 hours | 100 |
| 14,460 | 26 | 87% in 71 hours | 76 |
| 14,600 | 26 | 93% in 71 hours | 50 |
| 14,300 | 26 | 84% in 70 hours | 38 |
| 13,700 | 26 | 80% in 70 hours | 26 |
| 13,300 | 26 | 80% in 70 hours | 13 |
| 15,000 | 25 | 91% in 68 hours | 50 |

| Enzyme (U/ml) | M-3,6-diG (mg/ml) | Conversion to M-6-G |
|---|---|---|
| Experimental data for free L-11 in pH 3.8 acetate buffer | | |
| 53,400 | 9.8 (96%) | 90% in 18 hours |
| 53,500 | 9.9 (90%) | 84% in 18 hours |
| 52,900 | 10.8 (80%) | 73% in 18 hours |
| Experimental data for free L-11 in pH 3.8 citrate buffer | | |
| 54,800 | 10.9 (96%) | 46% in 18 hours |
| 52,200 | 10.6 (96%) | 42% in 23 hours |
| 53,500 | 10.1 (90%) | 68% in 18 hours |
| 51,000 | 9.8 (90%) | 70% in 23 hours |
| 53,400 | 9.6 (80%) | 73% in 18 hours |
| 55,000 | 10.1 (80%) | 72% in 23 hours |
| 51,200 | 10 (90%) | 94% in 24 hours |
| 59,000 | 10 (90%) | 90% in 24 hours |
| 70,000 | 102 (90%) | 46% in 24 hours |
| 8,200 | 13.7 (90%) | 78% in 24 hours |
| 8,200 | 1.2 (90%) | 100% in 13 hours |
| Experimental data for HA-4 in pH 5.0 citrate buffer | | |
| 71,200 | 106 (90%) | 46% in 24 hours |
| 5,600 | 17 (90%) | 58% in 24 hours |
| 5,500 | 1.4 (90%) | 100% in 24 hours |

Experimental data for various enzymes in citrate buffer

| Enzyme | Enzyme (U/ml) | M-3,6-diG (mg/ml) | Conversion to M-6-G |
|---|---|---|---|
| B-1 (pH 5.0) | 13,300 | 2.5 | 9% in 24 hours |
| B-3 (pH 5.0) | 5,600 | 1.5 | Low Conversion |
| B-10 (pH 5.0) | 13,600 | 2.0 | Low Conversion |
| Bovine insoluble (pH 5.0) | 3,000 | 1.1 | Low Conversion |
| S-1 (pH 3.8) | 500 | 10 | Low Conversion |
| H-5 (pH 5.0) | 3,000 | 1.4 | Low Conversion |
| Abalone (pH 3.8) | 1,400 | 15.8 | Low Conversion |
| Abalone (pH 3.8) | 8,800 | 16.7 | 38% in 24 hours |

Milligram scale synthesis of M-6-G using enzyme L-11

The enzyme (28.2 mg, 53,300 units) was dissolved in acetate buffer (1.0 ml, 0.1M pH 3.8) and the diglucuronide (9.8 mg, 14.6 μmol) added. The reaction mixture was placed in an orbital incubator at 30° C. and the reaction monitored by HPLC. After 18 hours analysis showed 90% conversion to M-6-G.

Gram scale synthesis of M-6-G using enzyme L-11

The enzyme (250.1 mg, 600,000 units) was dissolved in acetate buffer (40 ml, 0.1N pH 3.8) and the oxirane acrylic beads (2.02 g) added. The suspension was placed in an oribtal incubator at 30° C. for 30 minutes before the diglucuronide (1.00 g, 1.49 mmol) was added. The reaction was monitored by HPLC and stopped after 68 hours when analysis showed 91% conversion to M-6-G. Filtration of the resin beads with a Hirsch funnel yielded a cloudy solution, which was clarified through a HPLC solvent filter and evaporated in vacuo to a solid. Recrystallisation from aqueous methanol gave M-6-G as a white solid (175 mg, 25%)

$^1$H NMR (300 MHz, D$_2$O): δ 6.70 (d,J 8 Hz, H-2), 6.62 (d,J 8 Hz, H-1), 5.77 (bd,J 10 Hz, H-8), 5.30 (bd,J 10 Hz, H-7), 5.19 (d,J 6 Hz, H-5), 4.67 (d,J 8 Hz, H-1'), 4.54–4.46 (bs, H-6), 4.19–4.10 (bs, H-13), 3.68 (d,J 9 Hz, H-5'), 3.55–3.43 (m, H-4', 3'), 3.29 (dd,J 9 and 8 Hz, H-2'), 3.31 (d,J 18 Hz, H$_{eq}$-12), 2.92 (bs, NCH$_3$), 2.28 (td,J 13.5, 12, 4.5 Hz, H$_{ax}$-15), 2.07 (bd,J 12 Hz, H$_{eq}$-15)

We claim:

1. A method of making morphine-6-glucuronide comprising the selective enzymatic cleavage of the 3-glucuronide moiety in morphine-3, 6-diglucuronide or substituted morphine-3, 6-glucuronide using at least one β-glucuronidase, wherein the β-glucuronidase is obtained from any of the following: abalone molluse; the limpet patella vulgata; or helix aspersa.

2. A method as claimed in claim 1, wherein the β-glucuronidase is loaded onto one or more acrylic beads.

* * * * *